United States Patent [19]
Krug

[11] 4,074,577
[45] Feb. 21, 1978

[54] SAMPLING ASSEMBLY FOR TAKING A SAMPLE OF LIQUID AT A DESIRED LEVEL IN A TANK

[75] Inventor: John A. Krug, St. Charles, Mo.
[73] Assignee: ACF Industries, Incorporated, New York, N.Y.
[21] Appl. No.: 782,647
[22] Filed: Mar. 30, 1977
[51] Int. Cl.$^2$ ............................................. G01N 1/16
[52] U.S. Cl. ..................................... 73/421 B; 73/297
[58] Field of Search ...................... 73/297, 298, 421 B

[56] References Cited

U.S. PATENT DOCUMENTS

| | | | |
|---|---|---|---|
| 1,509,535 | 9/1924 | Werz | 73/297 |
| 2,090,514 | 8/1937 | Folmsbee | 73/297 |
| 2,440,230 | 4/1948 | Buttner | 73/297 |

*Primary Examiner*—S. Clement Swisher
*Attorney, Agent, or Firm*—Henry W. Cummings

[57] ABSTRACT

An assembly is provided for taking a sample from a desired level in a tank, including at least one tube extending from the outside of the tank to a selected level in the tank from where a sample is to be taken. The inner end of the tube is in fluid communication with a sampling chamber. The sampling chamber has an opening in its lower portion in communication with the inside of the tank through which liquid from the tank to be sampled may enter. The outer end of the tube is provided with a sampling valve for removing a sample from the tube. When the tank is not loaded, air enters the sampling chamber and the tube from within the tank and/or from the outside of the tank when the sampling valve is opened. The sampling valve is closed prior to loading the tank. The sampling chamber and the tube are sized such that the air pressure in the tube and in the sampling chamber prevent the liquid from entering the tube when the tank is filled. When the sampling valve is opened to take a sample the air pressure in the tube and in the sampling chamber is relieved. The pressure in the tank resulting from the weight of the lading and/or super-atmospheric pressure in the tank forces a liquid sample through the tube to the outside of the tank. A plurality of sampling assemblies may be provided each having a tube extending to a different level in the tank for taking samples from a plurality of levels in the tank. The outer ends of the sampling tubes, and the sampling valves are conveniently, though not necessarily, located at the bottom of the tank.

11 Claims, 6 Drawing Figures

SAMPLING ASSEMBLY FOR TAKING A SAMPLE OF LIQUID AT A DESIRED LEVEL IN A TANK

BACKGROUND OF THE INVENTION

This invention relates to an assembly for taking a liquid sample from one or more selected levels in a tank.

Previously arrangements for taking a liquid sample from a selected level in a tank have included a plurality of tubes extending to different depths in the tank from where it is desired to take a sample. Pressure in the tank or gravity may be used to obtain samples from the tubes. See for example, U.S. Pat. No. 2,090,514 (1937). If the tubes extend upwardly from the bottom of the tank, with drain valves in the bottom to remove the samples, the tubes fill up with liquid as the tank is filled. Thus a representative sample of the liquid at the particular level in the tank at the time the sample is taken is not obtained when the drain valves are opened. Furthermore, to completely unload the tank, the drain holes from all sampling tubes must be opened and the liquid collected.

Another sampling arrangement includes a tube extending vertically within the tank having an operator within the tube having a valve at its inner end which opens and closes the inner opening into the tube. Gravity or super-atmospheric pressure in the tank force a sample out when the valve is moved to the open position. See U.S. Pat. Nos. 1,638,333 and 2,404,087. However, if the valve and/or the operator becomes stuck the lading must be drained and the operator must enter the tank to repair and/or replace the damaged parts.

SUMMARY OF THE INVENTION

An assembly is provided for taking a liquid sample from a desired level in the tank, including at least one tube extending from the outside of the tank to a selected level in the tank from where a sample is to be taken. The inner end of the tube is in fluid communication with a sampling chamber. The sampling chamber has at least one opening in its lower portion in communication with the inside of the tank through which liquid from the tank to be sampled may enter. The outer end of the tube is provided with sampling valve means for removing a sample from the tube. When the tank is not loaded, air enters the sampling chamber and the tube from within the tank and/or from the outside of the tank when the sampling valve means is opened. The sampling valve means is closed prior to loading the tank. The sampling chamber and the tube are sized such that the air pressure in the tube and in the sampling chamber prevent the liquid from entering the tube as the tank is filled. When the sampling valve means is opened to take a sample, the air pressure in the tube and in the sampling chamber is relieved. The pressure in the tank resulting from the weight of the lading and/or the super-atmospheric pressure in the tank forces a liquid sample through the tube to the outside of the tank. A plurality of sampling assemblies may be provided each having a tube extending to a different level in the tank for taking samples from a plurality of levels in the tank. The outer ends of the sampling tubes, and the sampling valve means are conveniently, though not necessarily located at the bottom of the tank.

THE DRAWINGS

DESCRIPTION OF PREFERRED EMBODIMENT

Figure 1:
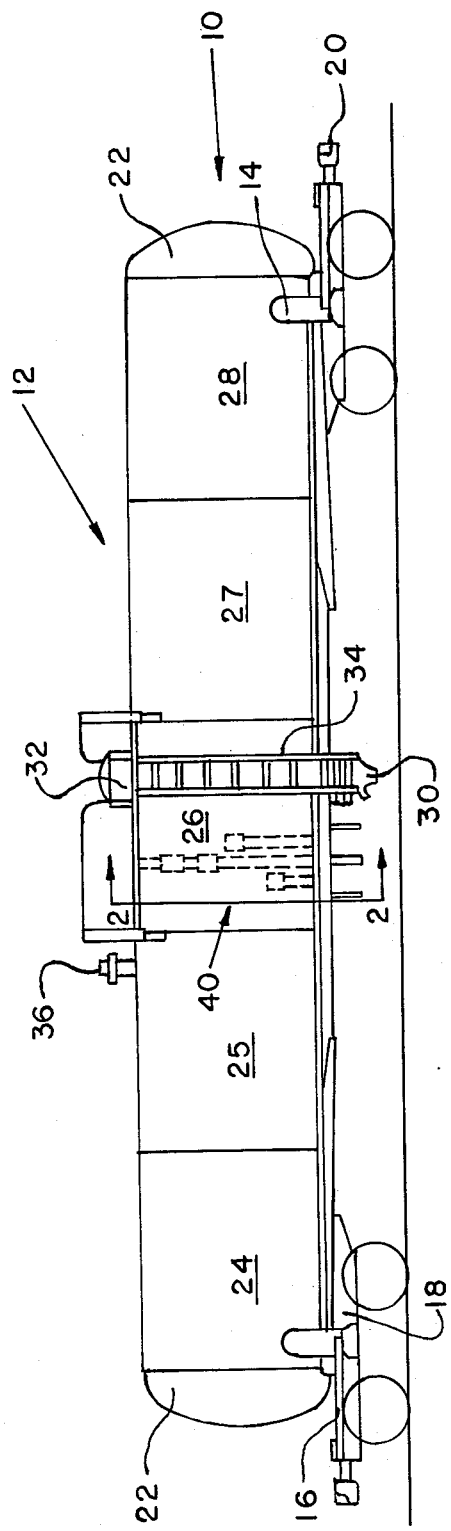
FIG. 1 is a side elevation of a railway tank car with which the sampling assembly of the present invention may be utilized.

The sampling assembly of the present invention may be utilized in a fixed storage tank, an overland tank truck, an intermodel tank container or in a container mounted in a ship. However, the sampling assembly of the present invention is particularly adapted for use in a railway tank car. Therefore the assembly will be described and illustrated in connection with its application to a railway tank car.

In the drawings, a railway tank car 10 is illustrated in which a tank 12 is mounted upon cradles 14 which are supported by stub sill 16 and trucks 18 at opposite ends of the car. A conventional coupler 20 and a draft gear (not shown) are mounted within the stub sills. The tank includes end portions 22 and tank sections 24, 25, 26, 27 and 28 welded together to form an integral tank.

The tank car may be loaded and/or unloaded through a bottom operated lading valve 30, for example, constructed according to the teachings of U.S. Pat. No. 3,981,481 granted Sept. 21, 1976, assigned to the same assignee as the present application, or according to the teachings of one or more of U.S. Pat. Nos. 3,227,101; 3,591,131; 3,661,355; or 3,721,424.

Normally an air outlet valve and a vacuum relief valve are provided on the top of the car within syphon housing 32. A ladder 34 is provided for the operator to climb to the top of the car to operate the air outlet valve when the tank is loaded. A safety vent 36 is also provided to prevent the tank from exploding in the event of pressure build up in the tank. For example, safety vent 36 may be constructed according to the teachings of U.S. Pat. No. 3,845,876, also assigned to the assignee of the present application.

Figure 2:
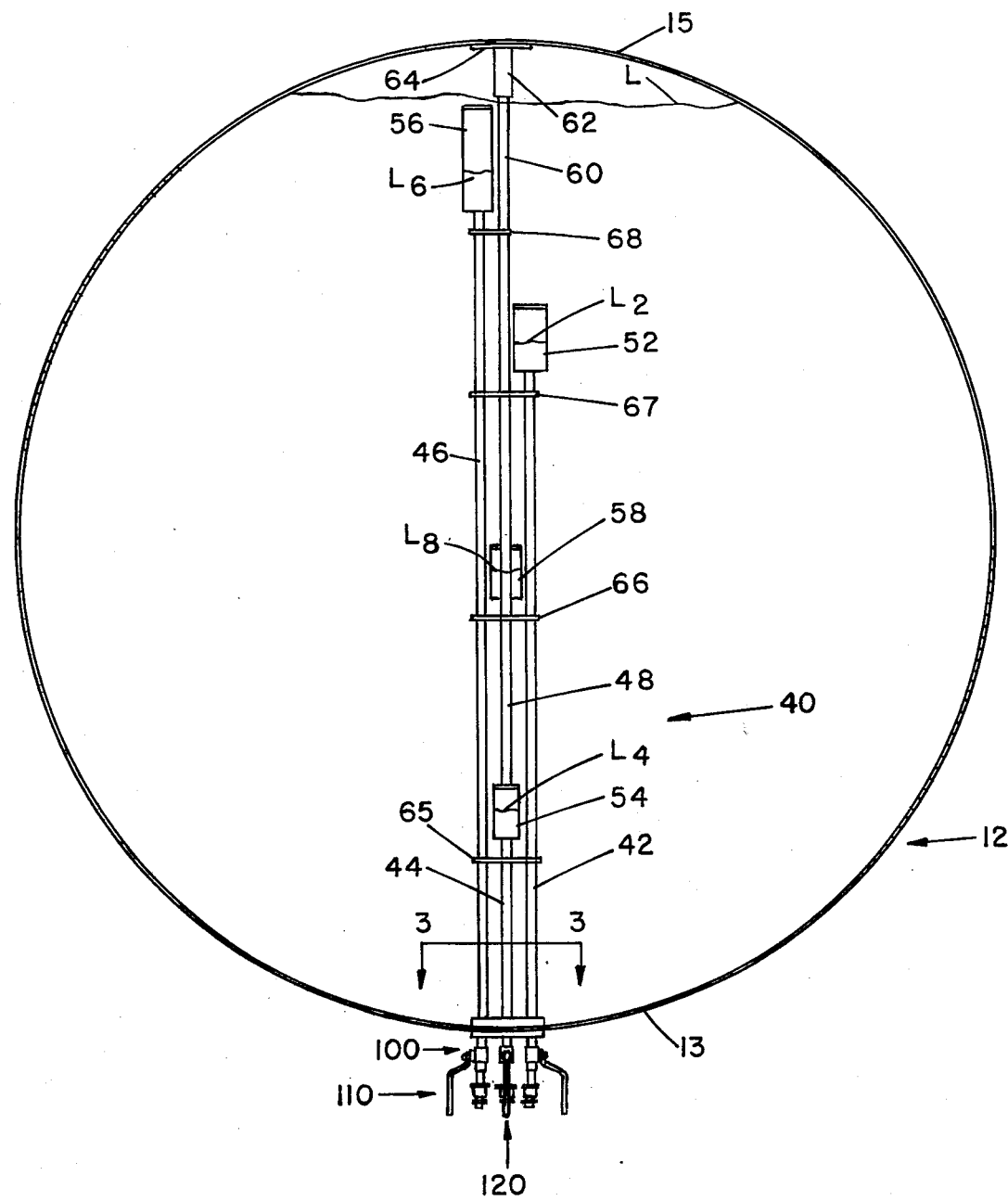
FIG. 2 is a sectional view looking in the direction of the arrows along the line 2—2 in FIG. 1.
Figure 6:
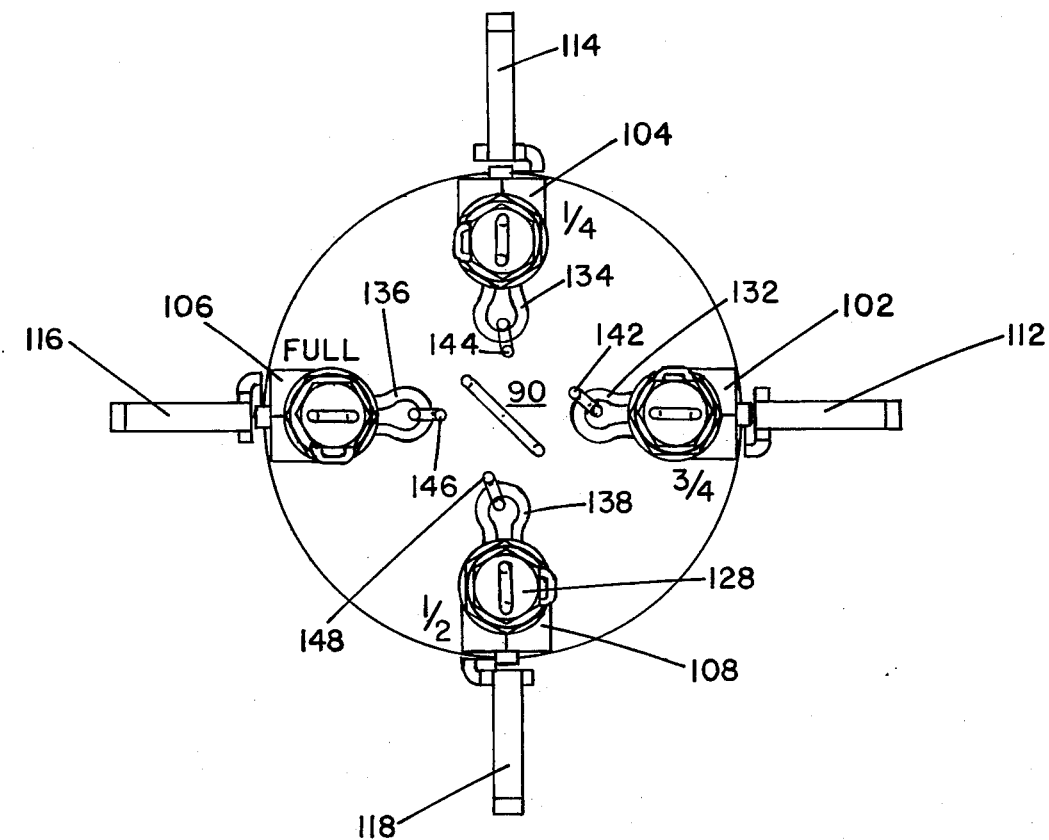
FIG. 6 is a bottom view looking in the direction of the arrows along the line 6—6 in FIG. 5.
Figure 3:
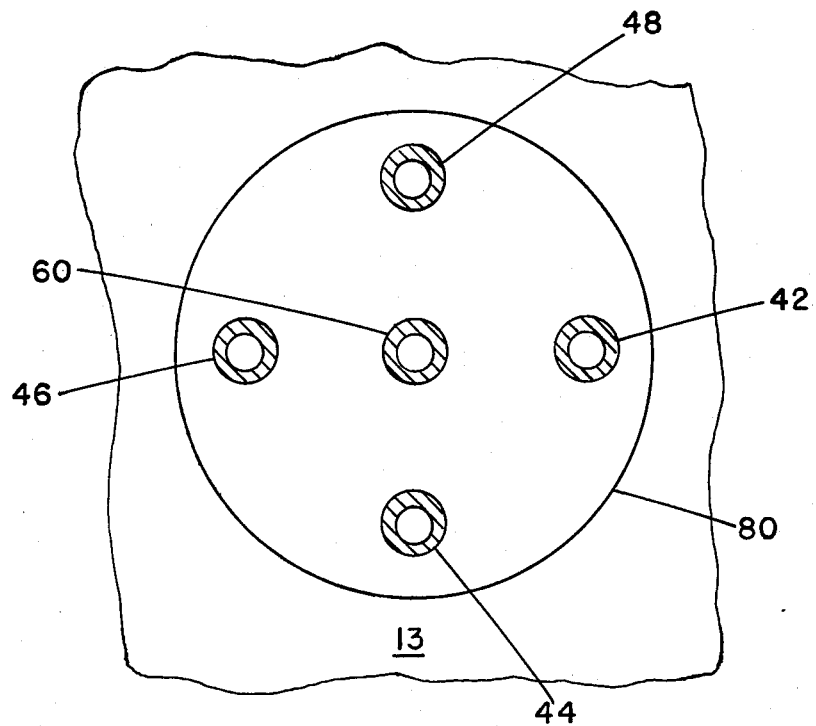
FIG. 3 is a sectional view looking in the direction of the arrows along the line 3—3 in FIG. 2.

The sampling assembly of the present invention is indicated generally at 40 in FIGS. 1 and 2. The sampling assembly includes a plurality of tubes 42, 44, 46 and 48 (FIG. 3) each rigidly attached to the bottom portion 13 of the tank 12 and extending to different levels in the tank so that samples from different levels of the tank may be obtained. At the inner end portion of each of the respective tubes, sampling chambers 52, 54, 56 and 58 are provided.

Furthermore, a center tube 60 extends all the way from the bottom of the tank to the top of the tank 15. A collar 62 is attached to the upper portion of the tank by means of a mounting plate 84 which is welded to the tank top 13. Center tube 60 is provided for reinforcement only. Vertically spaced brackets 65, 66, 67 and 68 are welded to center tube 60 and to the respective sampling tubes 42, 44, 46 and 48. With this arrangement the sampling assembly of the present invention is rigidly mounted within the tank 10.

Figure 4:
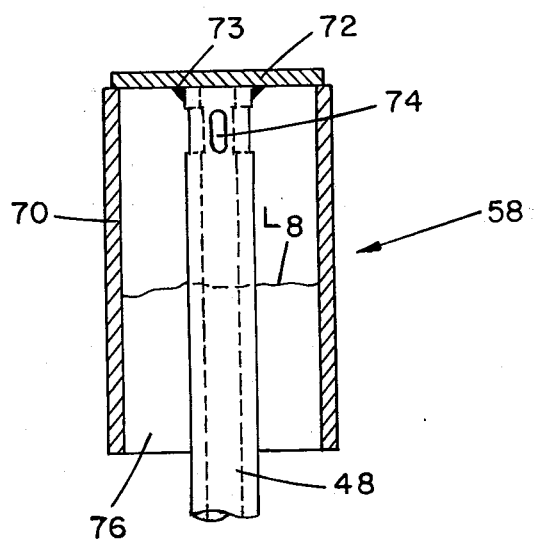
FIG. 4 is an enlarged sectional view illustrating the construction of the sampling chamber in the present invention.

Each of the sampling chambers 52, 54, 56 and 58 is constructed generally in the same manner. One of these sampling chambers 58 is illustrated in enlarged FIG. 4. The sampling chambers are conveniently cylindrical including a cylindrical wall portion 70 and a top 72 attached to the top of the cylindrical wall portion 70. The sampling tube 48 is rigidly attached to the sampling chamber top 72 by welding 73. Near its upper end the sampling tube 48 is provided with circumferentially spaced openings 74 which provide communication between the interior of the sampling chamber 58 and the hollow interior of the sampling tube 48. Sampling chamber 58 is open at the bottom as indicated at 76 to provide communication between the sampling chamber 58 and the interior of the tank.

Figure 5:
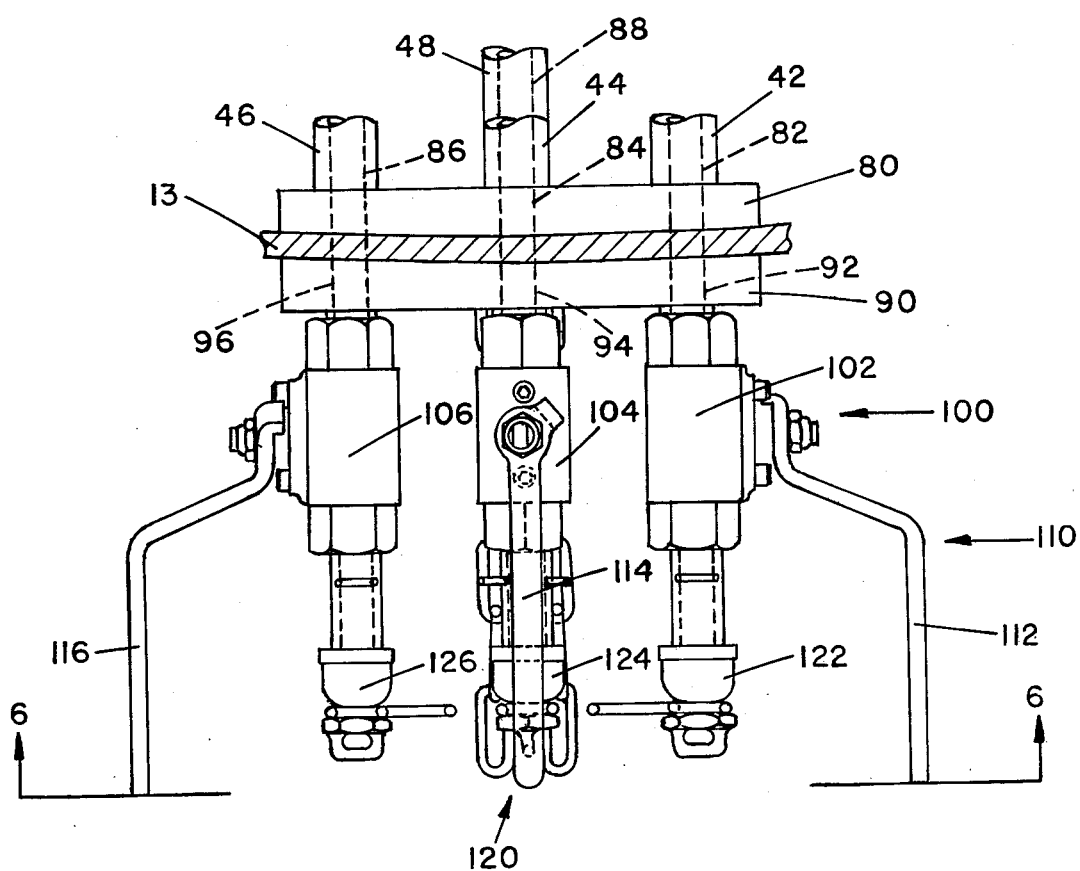
FIG. 5 is an enlarged side elevation view illustrating the sampling tube valve means and sampling tube cap means of the present invention.

As illustrated in FIG. 5 each of the tubes 42, 44, 46 and 48 may extend through and be welded to a mounting plate 80 having openings 82, 84, 86 and 88 therein corresponding to the respective tubes. The plate 80 in turn is welded to the bottom of the tank. An external mounting plate 90 may be provided externally of the tank having openings 92, 94, 96 and 98 which align with the respective openings in the tank bottom 13 and also with the openings in the internal mounting plate 80 through which tubes 42, 44, 46 and 48 pass to the outside of the tank.

Sampling tube valve means 100 is provided at the bottom of the tank including valve members 102, 104, 106 and 108 for each of the respective sampling tubes 42, 44, 46 and 48. Construction of the valve used for the sampling tubes does not form a part of this invention. Conventional valves may be used including ball valves, gate valves, and butterfly valves as examples. The sampling valve means is provided with appropriate sampling valve operating means indicated generally at 110 including handles 112, 114, 116 and 118, for operating each of the respective valves 102, 104, 106 and 108. Sampling tube cap means 120 is provided including caps 122, 124, 126 and 128 for each respective sampling tube 42, 44, 46 and 48. Each of the caps is provided with a chain 132, 134, 136 and 138 connected to respective lugs 142, 144, 146 and 148 rigidly attached to external mounting plate 90 to prevent the caps from being lost when they are removed for sampling.

The sampling assembly of the present invention operates as follows. Before the tank 12 is loaded caps 122, 124, 126 and/or 128 are removed and valves 102, 104, 106 and/or 108 respectively are opened to provide communication between the atmosphere and the respective sampling chambers 52, 54, 56 and/or 58. Valves 102, 104, 106 and/or 108 respectively are then closed. The tank is loaded with liquid by means of valve 30 in a conventional manner. Assuming the tank is filled, the liquid will assume a liquid level L indicated in FIG. 2. As the tank is filled, the lading will compress the air within the tubes 42, 44, 46 and 48 and the air within chambers 52, 54, 56 and 58. The air in the lower sampling tubes and sampling chambers will be compressed a greater extent than the air in the sampling tubes and sampling chambers located higher in the tank. In compressing the air in the sampling chambers and sampling tubes, the lading will enter at least the lower portion of the sampling chambers 52, 54, 56 and 58, as indicated at $L_2$, $L_4$, $L_6$ and $L_8$ respectively. However, the sampling tubes and the sampling chambers are sized such that for a given lading and tank pressure the liquid will not sufficiently compress the air in the sampling tubes and sampling chambers when the tank is fully loaded that the liquid will enter the sampling tubes, ie. through openings 74, when the tank is full.

The volume of the sampling tubes and sampling chambers is related to the lading pressure and the super-atmospheric pressure in the tank in the following manner.

For instance assume that the volume of sampling tube 48 is 5 in$^3$ and the volume of sampling chamber 58 is 45 in$^3$. By known gas laws, assuming constant temperature, $P_1V_1$ at loading ($P_1$ equals atmosphere pressure of 14.7psi and $V_1$ equals total volume of 50in$^3$) must equal $P_2V_2$ at time of unloading ($P_2$ equals pressure in tank from lading pressure and super-atmospheric pressure and $V_2$ equals final volume of compressed gas in the tubes). Assuming $P_2$ = 100 psi, by the equation $P_1V_1 = P_2V_2$, $V_2$ = 14.7psi × 50in$^3$/100psi = 7.35 in$^3$. Hence at time of unloading the tube having a volume of 5 in$^3$ will only contain air and the chamber will be filled with liquid except for 7.35 − 5.00 = 2.35 in$^3$ at the top. It should be noted that the tubes and chambers can also be sized to account for temperature variables (at loading) $P_1V_1/T_1 = P_2V_2/T_2$ (at unloading); with $T_1$ and $T_2$ Kelvin Temperature Units.

The liquid may remain for an indefinite period in the loaded condition illustrated in FIG. 2 either in a fixed storage tank or in a transportation container and/or railway car until such time at it is desired to take a sample from one of the levels where the sampling tubes and sampling chambers are located.

When it is desired to take a sample of one or more levels in the tank, the appropriate cap(s) 132, 134, 136 and/or 138 is removed and a suitable container placed therebelow to receive the sample. Then the appropriate valve 102, 104, 106 and/or 108 is opened. The pressure of the liquid in the tank and/or above atmospheric pressure in the tank will force a sample upwardly into and through the openings at the end portion of the sampling tubes (for instance 74 in FIG. 4) and then the sample will pass out of the tube. To the extent that inner portions are above outer portions of the tube; sample removal will be aided by gravity if the tube is partially vertical. When a sufficiently large sample is obtained, the appropriate valve(s) 102, 104, 106 and 108 is closed.

When desired, the tank is unloaded in a conventional manner through lading valve 30. To completely remove all of the liquid from the tank it is necessary to remove the caps and open the valves from those tubes only from which a sample was taken after the tank was loaded. The liquid obtained from the sampling tube is of the same composition as when the sample was taken. After the tank is unloaded each of the sampling tube valves are preferably opened to be certain that no liquid remains therein.

The above described loading and sampling cycle may be repeated.

It will be apparent that the sampling assembly of the present invention has the following advantages. The sampling chamber prevents liquid from entering the sampling tube until such time it is desired to take a sample. Therefore the sample obtained from each sampling tube is a sample of the liquid at that level in the tank at the time the sample is taken. A sample may be taken of a desired level, only, and the sample obtained will be representative of the liquid composition of that level at the time the sample is taken. Additionally the sampling assembly has no moving parts or valves inside the tank which could become inoperative and prevent operation of the device. The sampling valve means may be conventional, commercially available shelf items, and if repair or replacement is necessary, it is not necessary to enter the tank for this operation.

What is claimed:

1. A sampling assembly for taking a sample from a desired level in a tank comprising:

at least one tube extending from the outside of the tank to a selected level within the tank; the inner end of said tube being in fluid communication with a sampling chamber; said sampling chamber having a sampling chamber opening in its lower portion in communication with the inside of the tank; sampling valve means for removing a sample from the tube located at the outer end portion of the tube; whereby when the tank is not loaded, air enters the sampling chamber and the tube from within the tank through said sampling chamber opening and/or from the outside of the tank when the sampling valve is open; the volume of said sampling chamber and said tube being such that air is compressed in the tube and in the sampling chamber as the tank is filled with liquid; said compressed air preventing the liquid from entering the tube through said sampling chamber opening when the tank is being loaded with liquid; and whereby when the sampling valve means is opened to take a sample, the air pressure in the tube and in the sampling chamber is relieved, and the pressure in the tank resulting from the weight of the lading and/or super-atmospheric pressure in the tank forces a liquid sample through the tube to the outside of the tank.

2. A sampling assembly according to claim 1 wherein a plurality of sampling assemblies are provided, each having a tube extending to a different level in the tank for taking samples from a plurality of levels in the tank.

3. A sampling assembly according to claim 1 wherein the outer end of the sampling tube, and the sampling valve means are located at the bottom of the tank.

4. A sampling assembly according to claim 1 wherein said sampling chamber is open at the bottom to provide fluid communication with the tank.

5. A sampling assembly according to claim 1 wherein a valve cap is provided for attachment to the outer end of said tube.

6. In a railway tank car including a tank body supported by longitudinally spaced trucks having wheels for moving the car along the railroad track; a lading opening in the tank body; lading valve means located adjacent the opening for opening and closing the lading opening; the improvement comprising:

a sampling assembly for taking a sample from a desired level in a tank comprising:

at least one tube extending from the outside of the tank to a selected level within the tank; the inner end of said tube being in fluid communication with a sampling chamber; said sampling chamber having a sampling chamber opening in its lower portion in communication with the inside of the tank; sampling valve means for removing a sample from the tube located at the outer end portion of the tube; whereby when the tank is not loaded, air enters the sampling chamber and the tube from within the tank through said sampling chamber opening and/or from the outside of the tank when the sampling valve is open; the volume of said sampling chamber and said tube being such that air is compressed in the tube and in the sampling chamber as the tank is filled with liquid; said compressed air preventing the liquid from entering the tube through said sampling chamber opening when the tank is being loaded with liquid; and whereby when the sampling valve means is opened to take a sample, the air pressure in the tube and in the sampling chamber is relieved, and the pressure in the tank resulting from the weight of the lading and/or super-atmospheric pressure in the tank forces a liquid sample through the tube to the outside of the tank.

7. A tank car according to claim 6 wherein a plurality of sampling assemblies are provided, each having a tube extending to a different level in the tank for taking samples from a plurality of levels in the tank.

8. A tank car according to claim 7 wherein the outer ends of the sampling tube, and the sampling valve means are located at the bottom of the tank.

9. A tank car according to claim 8 wherein the lading opening and the lading valve means are also located at the bottom of the tank.

10. A method for taking a sample from a desired level in a tank comprising:

providing at least one tube extending from the outside of the tank to a selected level in the tank; providing a sampling chamber in fluid communication with the inner end of the tube; the sampling chamber having an opening in its lower portion in communication with the inside of the tank through which liquid from the tank to be sampled may enter; providing the outer end of the tube with a sampling valve for removing a sample from the tube; allowing air to enter the sampling chamber and the tube from within the tank and/or from the outside of the tank when the sampling valve is opened; when the tank is not loaded closing the sampling valve; loading the tank with liquid and thereby compressing air in the sampling chamber and in the tube; providing the sampling chamber and the tube of volume such that the air pressure in the tube and in the sampling chamber prevent the liquid from entering the tube as the tank is loaded; opening the sampling valve and thereby relieving the air pressure in the tube and in the sampling chamber, whereby the pressure in the tank resulting from the weight of the lading and/or super-atmospheric pressure in the tank will force a liquid sample through the tube to the outside of the tank.

11. A method according to claim 10 including providing a plurality of sampling assemblies, each having a tube extending to a different level in the tank, and taking samples from a plurality of levels in the tank according to the process of claim 10.

* * * * *